United States Patent [19]

Petrofsky

[11] Patent Number: 4,711,242

[45] Date of Patent: Dec. 8, 1987

[54] CONTROL SYSTEM FOR KNEE JOINT

[75] Inventor: Jerrold S. Petrofsky, Beavercreek, Ohio

[73] Assignee: Wright State University, Dayton, Ohio

[21] Appl. No.: 829,722

[22] Filed: Feb. 18, 1986

[51] Int. Cl.⁴ .............................................. A61N 1/32
[52] U.S. Cl. ........................... 128/419 R; 128/423 W
[58] Field of Search .................... 128/419 R, 421–423, 128/80 C, 80 F, 80; 623/44, 23, 24

[56] References Cited

U.S. PATENT DOCUMENTS

| | | | |
|---|---|---|---|
| 2,883,982 | 4/1959 | Rainey | 128/80 C |
| 3,417,409 | 12/1968 | Prahl | 623/44 |
| 3,453,663 | 7/1969 | Minor | 623/44 |
| 3,799,159 | 3/1974 | Scott | 128/80 C |
| 3,826,251 | 6/1974 | Ross | 623/44 |
| 4,457,047 | 7/1984 | Lautenschläger | 16/288 |
| 4,492,233 | 1/1985 | Petrofsky et al. | 128/421 |
| 4,557,257 | 12/1985 | Fernandez et al. | 128/80 G |
| 4,569,352 | 2/1986 | Petrofsky et al. | 128/423 W |
| 4,586,510 | 5/1986 | Glaser | 128/423 W |

FOREIGN PATENT DOCUMENTS

| | | | |
|---|---|---|---|
| 719635 | 3/1980 | U.S.S.R. | 128/782 |
| 736975 | 5/1980 | U.S.S.R. | 128/80 G |
| 740255 | 6/1980 | U.S.S.R. | 128/423 W |

OTHER PUBLICATIONS

"A Microprocessor Based Portable Functional Electrical Stimulation System" by J. Buckett et al., Ann. Conf. on Rehab. Eng.; Sand Diego, 1983, pp. 72–74.

"A Motorized Orthotic Shoe for Submaximal Assist", by Cameron et al., Dig. of the Int. Electrical Electronics, Conf. & Expo, Toronto, Canada, 10/79.

"Effect of Gradually Modulated Electrical Stimulation on the Plasticity of Artificially Evoked Movements", Stanic et al., Mol. & Biol. Eng. & Comput., 1/77, vol. 15; pp. 62–66.

Petrofsky, Jerrold S., et al., U.S. Patent Appln. Ser. No. 671,805, filed 11/15/84. "Feedback Control System for Walking."

Petrofsky, Jerrold S., et al., "Closed-Loop Control of Skeletal Muscle." Dayton, Ohio: Wright State Univ., Sep. 1984.

Grady, Denise. "Walking Away from Paralysis." *Discover*, May 1981.

Liberson, W. T., et al. "Functional Electrotherapy: Stimulation of the Peroneal Nerve Synchronized with the Swing Phase of the Gait of Hemiplegic Patients." Read at 3rd Int'l Cong. of Phy. Medicine, Washington, D.C., Aug. 25, 1960.

Strojnik, P., et al. "Programmed Six-Channel Electrical Stimulator for Complex Stimulation of Leg Muscles During Walking." IEEE Transactions on Biomedical Engineering, Feb. 1979, pp. 112–116.

Douglas, Roy, et al., "The LSU Reciprocation-Gait Orthosis." *Orthopedics*, Jul. 1983, pp. 834–839.

*Primary Examiner*—William E. Kamm
*Assistant Examiner*—David Shay
*Attorney, Agent, or Firm*—Biebel, French & Nauman

[57] ABSTRACT

A system for controlling the movement of a human knee joint during stimulated flexion thereof. The system includes a brace having an over-center hinge at the knee joint. This hinge causes the knee joint to lock under load when the hinge is opened less than a predetermined angle. A sensor senses the angle of opening of the hinge joint and generates a corresponding sensing signal for use by a computer connected for controlling the stimulation of the knee. The computer is programmed for avoiding increases in the stimulation signal when the hinge joint has an angle of opening which is less than some predetermined angle greater than zero and not greater than the critical angle of the hinge.

8 Claims, 19 Drawing Figures

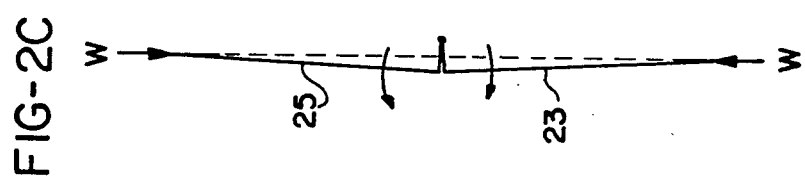
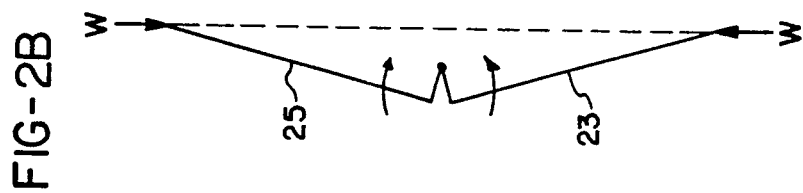
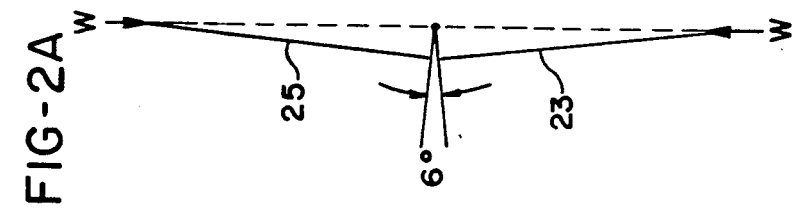
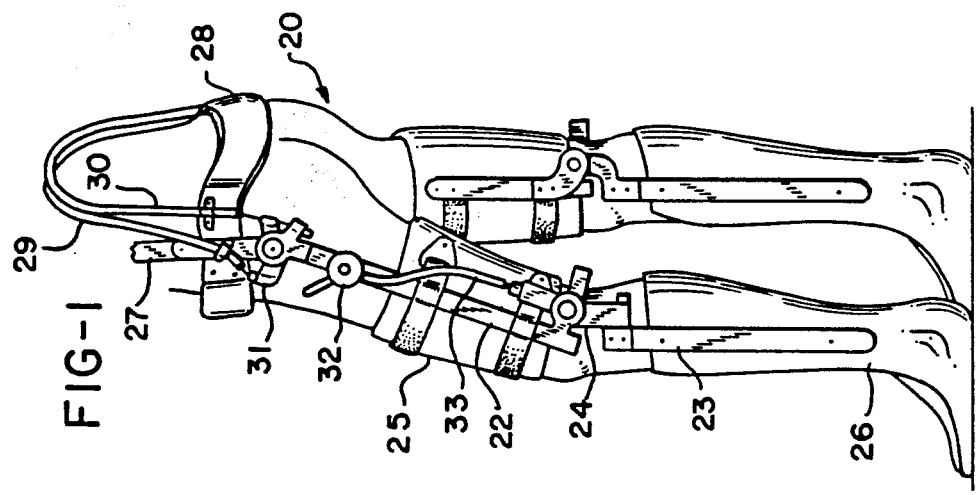

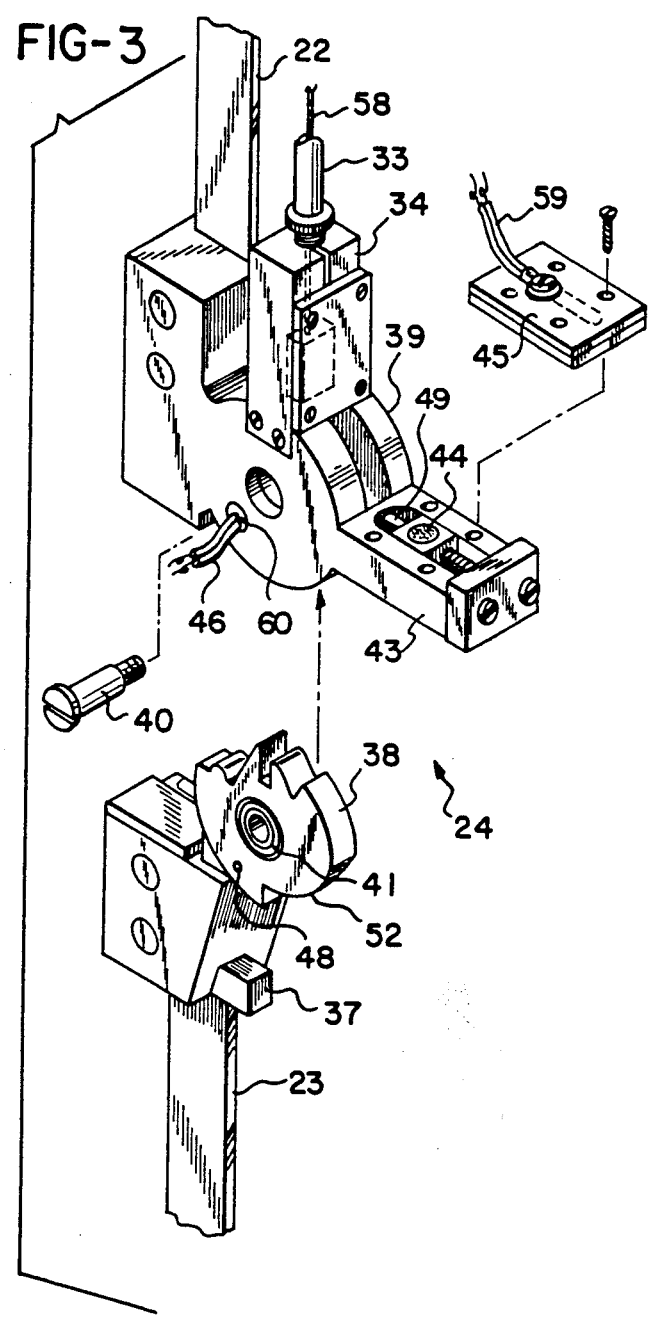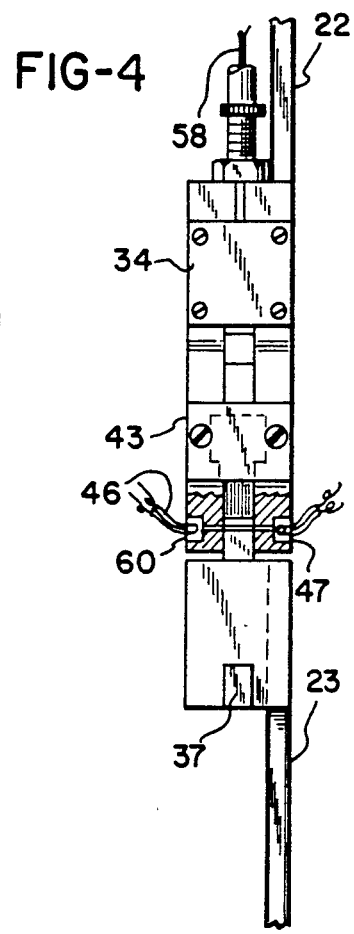

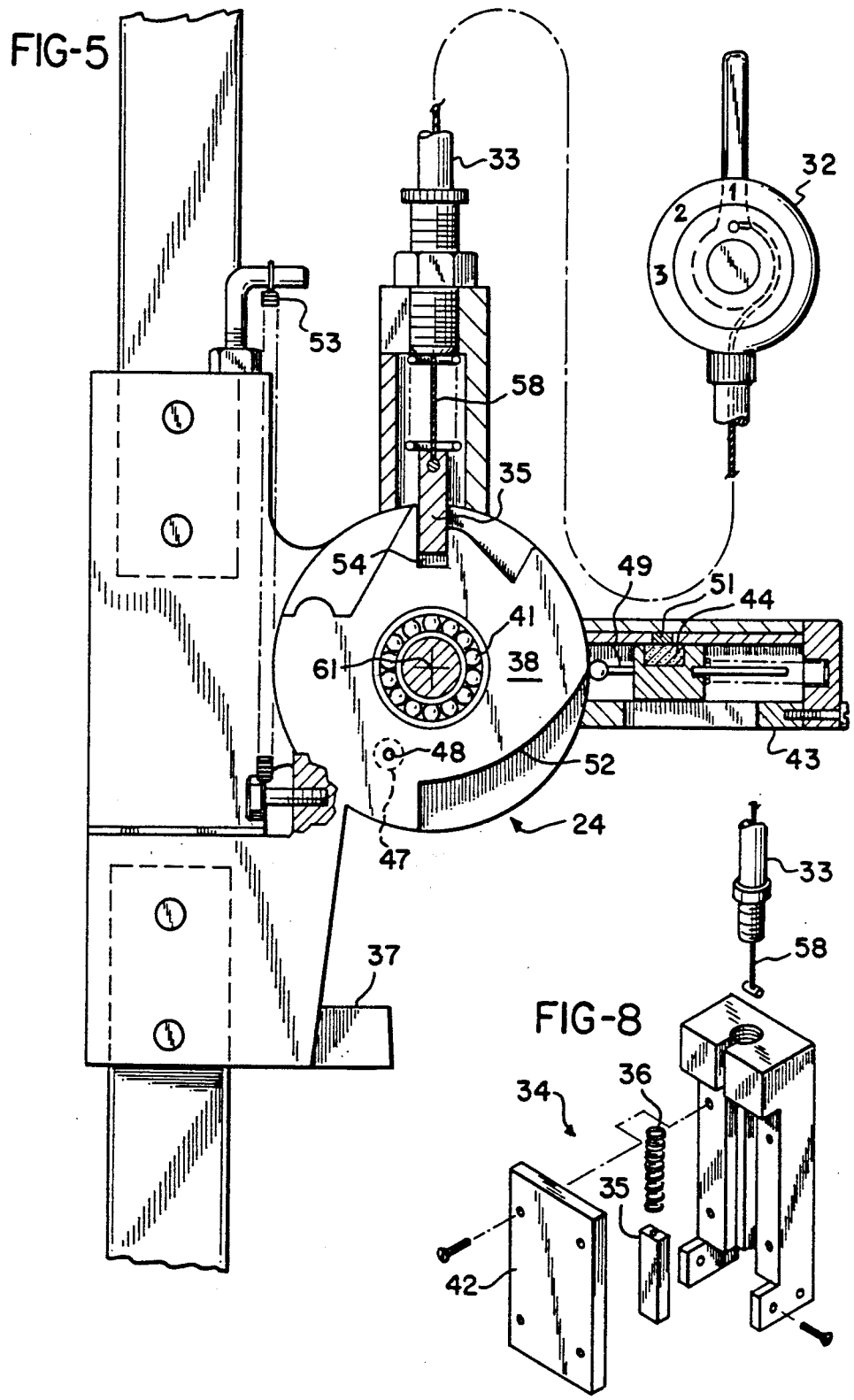

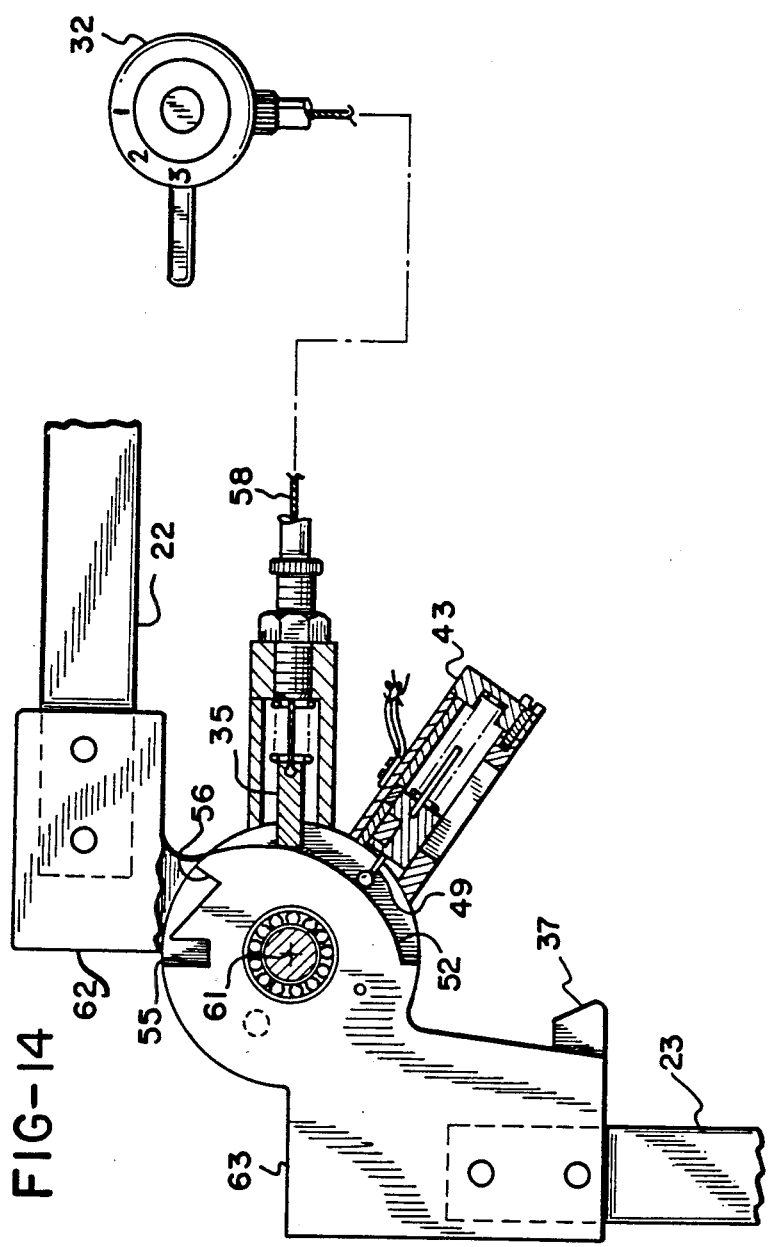

CONTROL SYSTEM FOR KNEE JOINT

BACKGROUND OF THE INVENTION

This invention relates to the field of assisted walking for handicapped persons. It relates more particularly to walking assistance systems of the general type described by Petrofsky et al. in U.S. application Ser. No. 671,805, filed Nov. 15, 1984, and in a paper entitled "Feedback Control System for Walking in Man," Petrofsky et al., *COMPUT. BIOL. MED.* 14:135–149, 1984. Such systems utilize stimulation devices of the general type described in Petrofsky et al. U.S. Pat. No. 4,492,233 for stimulation of the legs of a handicapped person to produce a walking movement. They also utilize braces which may be of the type shown in Ser. No. 671,805 or of the reciprocating-gait type as described in a paper by Douglas et al. entitled "The LSU Reciprocation-Gait Orthosis," *Orthopedics*, July 1983, pp. 834–839. The present invention relates particularly to apparatus and method for controlling knee joint flexion in such walking assistance systems.

One of the problems with the above mentioned walking assistance systems is that smooth knee joint control has been difficult to obtain. The difficulty lies in the fact that no practical system exists for measuring the tension in the tendons when the knee is locked. Currently available sensors only measure the knee flexion angle. This has created an end looping problem when the computing system has attempted to achieve a fully extended knee attitude through use of a flexion angle sensor in closed loop control. Since negative flexion angles cannot be achieved, the flexion angle sensor never senses positive values thereof. The computer therefore must stimulate the flexion control muscles using control signals based upon single-sided sensor information. The control problem is particularly complicated since the stimulation control signal may require a maximum value for maintenance of a flexion angle of zero degrees.

SUMMARY OF THE INVENTION

This invention provides improved knee joint control in a walking assistance system by providing a gravity lock brace having an over-center hinge. The hinge opens when the knee flexes but tends to lock under a vertically applied load, if opened less than a first predetermined angle when the load is applied. A sensor senses the angle of opening of the hinge joint and generates a corresponding sensing signal for transmission to a control means. The control means generates a reference signal representing a desired value for the opening angle of the hinge and produces a command signal related to the difference between the sensing signal and the reference signal. The command signal is non-responsive to changes in the sensing signal when the angle of opening is less than a second predetermined angle greater than zero and not greater than the first predetermined angle. Stimulation means are provided which are responsive to the command signal for stimulating the knee extension muscles. Thus the control means stimulates the leg muscles to extend the knee joint only until such time as the opening angle of the over-center hinge is within a range wherein gravity locking commences. At this point the control means ceases to command increasing knee joint extension.

It is therefore an object of this invention to provide apparatus and method for improved knee joint control in a walking assistance system.

Other objects and advantages of the invention will be apparent from the following description, the accompanying drawings and the appended claims.

BRIEF DESCRIPTION OF THE DRAWINGS

FIG. 1 is a pictorial illustration of a pair of reciprocating gait leg braces equipped with over-center hinges at the knee joints;

FIG. 2A through 2C are schematic illustrations of the action of forces applied to over-center hinges positioned at three different opening angles;

FIG. 3 is a partially exploded perspective view of a hinge assembly for knee joint control;

FIG. 4 is a partially cut-away end elevation view of the hinge assembly of FIG. 3;

FIG. 5 is a partially cut-away side elevation view of a hinge assembly locked in a fully closed position;

FIG. 8 is an exploded perspective view of a pin housing for the hinge assembly of the preceding figures;

FIG. 14 is a partially cut-away side elevation view of a hinge assembly in an alternative embodiment.

DESCRIPTION OF THE PREFERRED EMBODIMENT

Figure 6:
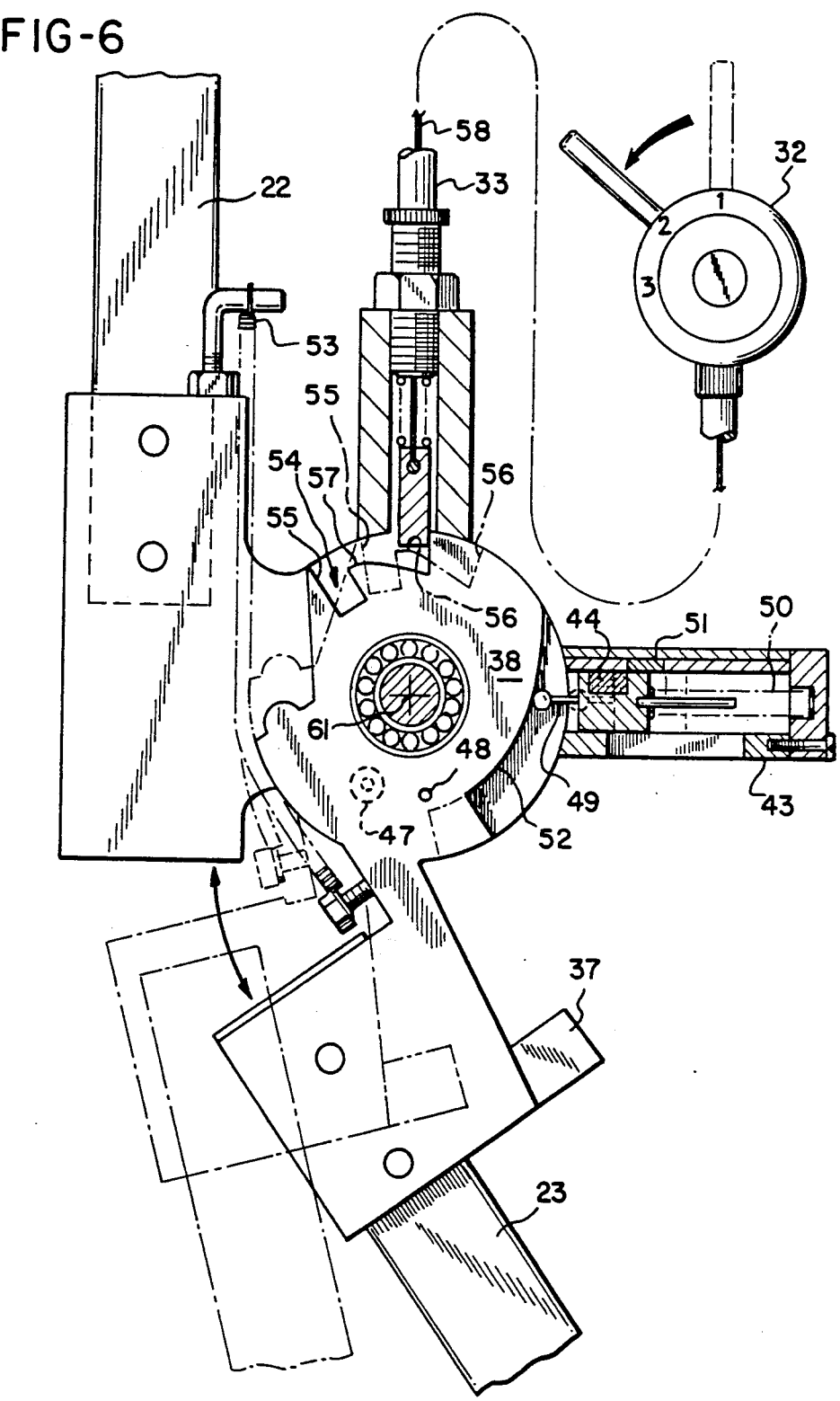
FIG. 6 is a partially cut-away side elevation view of a hinge assembly during knee flexion within a predetermined range.

Knee joint control in accordance with the present invention may be carried out in association with a walking assistance system including a pair of reciprocating-gait braces 20 as generally illustrated in FIG. 1. The structural details of such braces are described in the above noted paper appearing in *Orthopedics*. For the present purposes it is sufficient to note that the braces comprise a pair of leg support structures interconnected by a forward hip control cable 29 and a rearward hip control cable 30 at joints 31, 31 (only one of the joints being visible in FIG. 1). Cables 29 and 30 are attached to joints 31, 31 in such a manner as to produce extension of a hip when the weight of the wearer is placed on the opposite hip. Movement of the legs is stimulated by a series of transcutaneous electrodes 172 mounted in an electrode garment 166 (FIG. 12) operating under computer control.

Braces 20 also comprise a chest strap (not shown) and a pelvic band 28. Connected to the chest strap and to pelvic band 28 on each side thereof are a thoracic extension rod 27, an upper leg support rod 22 and a lower leg support rod 23. Support rods 22 and 23 are joined by an over-center hinge assembly 24 which opens as the knee joint flexes. Upper support rod 22 is attached to the upper leg of the wearer by a thigh support 25, while lower support rod 23 is attached to the lower leg by an ankle-foot orthosis 26. Pivotal movement of hinge assembly 24 is selectively controlled by a pin positioning cable 33 and a cable control 32.

As illustrated in FIG. 1, hinge assembly 24 is positioned on the outside of the left leg. A similar hinge assembly is positioned on the outside of the right leg. Both such hinge assemblies are assisted in their action by hinge assemblies placed on the insides of the legs. These latter hinge assemblies may be over-center hinge assemblies of conventional design.

While over-center hinge assemblies are well known, they generally are not over-centered to quite the extent that is preferred in connection with the practice of this invention. Preferably the hinge assemblies should be over-centered to such an extent as to be neutrally stable at an opening angle of about 6°, as generally illustrated in FIG. 2A. For opening angles greater than about 6° a vertically applied load on the joint produces further opening as illustrated in FIG. 2B. When the opening angle is smaller than about 6°, the load on the joint decreases the angle thereby producing a gravity lock as illustrated in FIG. 2C.

Figure 7:
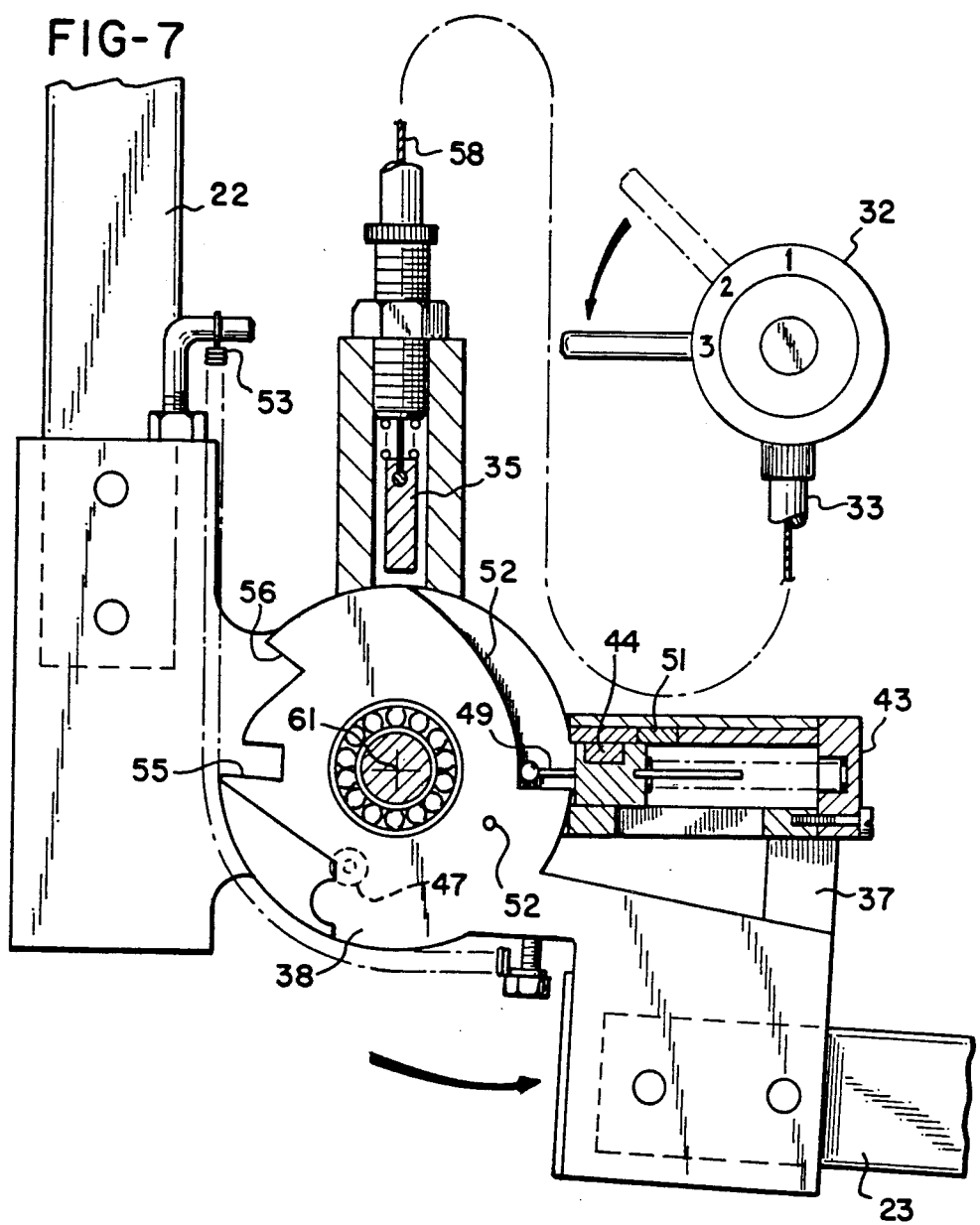
FIG. 7 is a partially cut-away side elevation view of a hinge assembly during knee flexion outside the predetermined range of FIG. 6.

Hinge assembly 24 may be locked as illustrated in FIG. 5 or selectively limited in its pivotal movement as illustrated in FIG. 6. When the orthosis is locked, the leg of the wearer is maintained in a fully extended attitude. Unlocking of the hinge permits unrestricted flexion up to a predetermined limit which may conveniently be on the order of about 34°. Preferably, hinge assembly 24 is further configured for selectively permitting unrestricted flexion up to a larger angle on the order of about 87° as illustrated in FIG. 7. This provides a backup safety feature for a wearer who has not developed complete confidence in the stimulation control system.

Hinge assembly 24 is constructed as generally illustrated in FIGS. 3 and 4. Thus it comprises a cam member 38 secured to the upper end of lower support rod 23. Cam member 38 is fitted with a ball bearing 41 for pivotal movement about an axis 61 which is laterally displaced from the center line of lower support rod 23.

Cam member 38 is received in a cam housing 39 mounted at the lower end of upper support rod 22. A pivot pin 40 passes through ball bearing 41 to secure cam member 38 within cam housing 39.

There is a pin housing 34 mounted on cam housing 39 directly above pivot pin 40. Pin housing 34 provides a sliding support for a pin 35, as illustrated in FIG. 8. Pin 35 is selectively positioned within housing 34 by controlled movement of a cable 58 carried within cable assembly 33. Pin 35 is biased against an enlarged end of cable 58 by a spring 36. Pin housing 34 is closed out by a cover plate 42.

Cam housing 39 also has a housing extension 43 which houses a transducer for measuring the opening angle of hinge assembly 24. The angle, so measured, is treated by the system as being equivalent to the knee flexion angle. Preferably the angle transducer comprises a permanent magnet 44 mounted on a cam follower 49 and a Hall effect transducer 51 (FIG. 6) secured to a cover plate 45. A spring 50 maintains cam follower 49 in contact against a cam surface 52 on cam member 38. Hall effect transducer 51 senses the movement of magnet 44 as cam follower 49 follows cam surface 52 and provides an electrical output signal indicative thereof. The output signal is supplied to a pair of electrical leads 59 for transmission to a microprocessor as hereinafter described. The microprocessor uses the output signal as a measure of flexion angle of the knee.

Cam housing 39 may also be provided with a light emitting diode 47 and a photodetector 60 mounted on opposite sides of cam member 38. Cam member 38 has a small aperture 48 which is in alignment with LED 47 and photodetector 60 when hinge assembly 24 is fully closed (Figs. 4 and 5). In this position photosensor 60 provides a "knee-lock" signal on line 46 for use by the microprocessor.

When hinge assembly 24 is in the fully closed position, cable control 32 may be placed in position No. 1, as illustrated in FIG. 5. In this position cable 58 urges pin 35 downwardly into a slot 54 in cam member 38. This locks the knee of the wearer in a fully extended attitude to accommodate standing for a prolonged period of time.

When the wearer desires to free his knee joints for stimulated walking he may position cable control 32 in position No. 2 (FIG. 6). In position No. 2 pin 35 is raised upwardly above a hump 57 in cam member 38 and is positioned within a pocket defined between a pair of end walls 55 and 56. This allows approximately 34° of unrestricted flexion. However, in the event of any stimulation failure pin 35 will be forced into contact against wall 56 to prevent collapsing of the wearer's legs.

If the wearer desires to assume a seated posture then cable control 32 may be placed in the position illustrated in FIG. 7. In this position pin 35 is raised clear of all obstructions on cam member 38. Hinge assembly 24 then may rotate approximately 87° until stop member 37 comes into contact with the lower surface of housing extension 43.

FIG. 14 illustrates a hinge assembly in an alternative embodiment with like reference numerals used to designate elements corresponding to elements illustrated in the above described embodiment. In the alternative embodiment, the housing extension 43 is repositioned to permit more than 90° of angular rotation between upper support rod 22 and lower support rod 23. This permits the wearer to lean forward for better center-of-gravity positioning prior to rising from a sitting to a standing position. Also in the alternative embodiment, abutting faces 62 and 63 of support rods 22 and 23, respectively, are placed in alignment with pivot axis 61 for better brace positioning. It will be observed that in this embodiment cam surface 52 is extended for accommodation of the increased angular movement.

Figure 9:
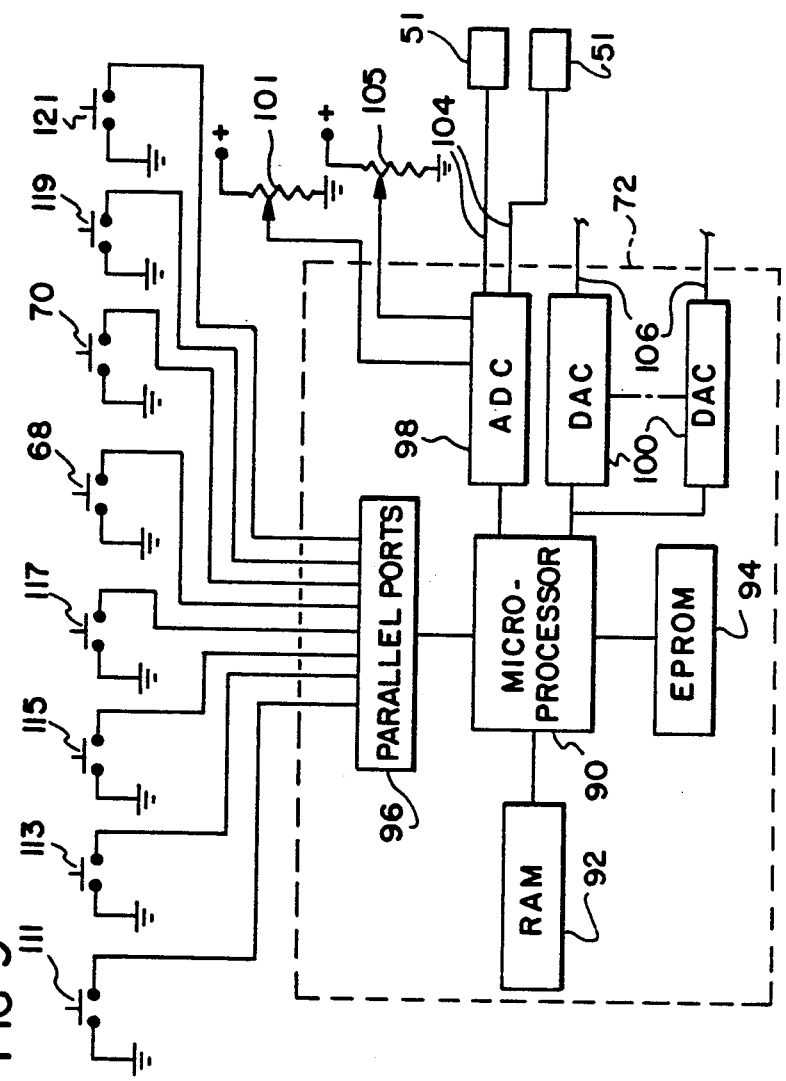
FIG. 9 is a block diagram of a microprocessor system for walking assistance.
Figure 10:
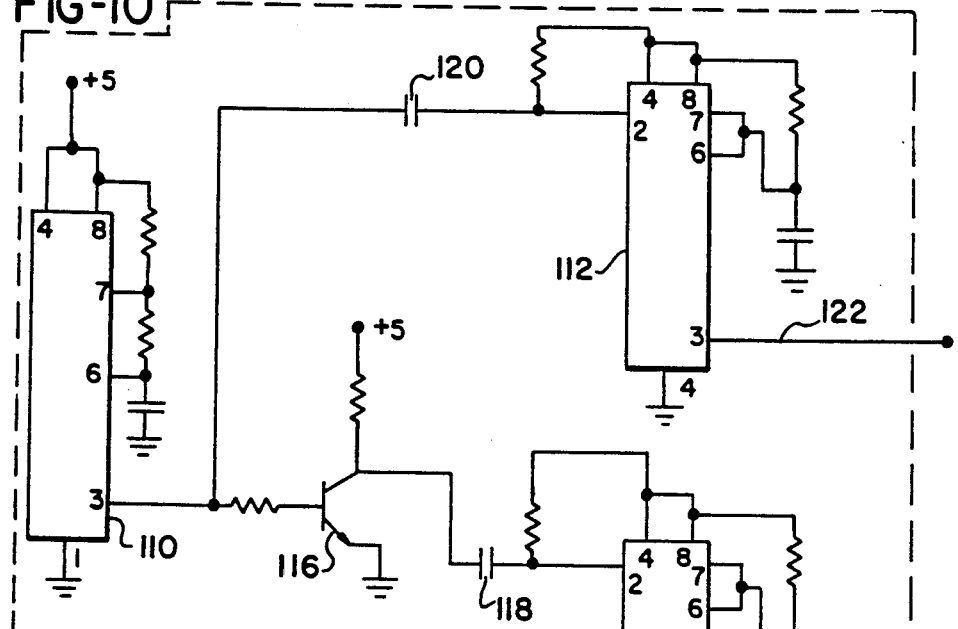
FIG. 10 is a schematic diagram of a pulse generator.
Figure 11:
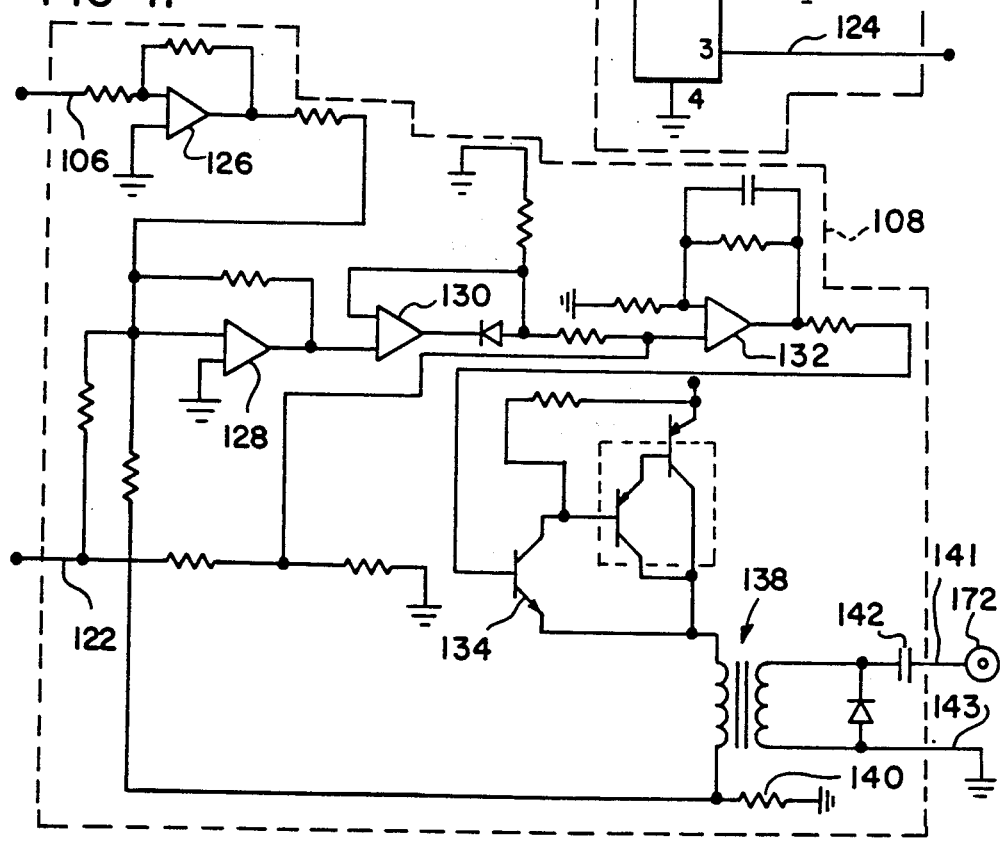
FIG. 11 is a schematic diagram of a stimulation driving circuit.

Electrical controls for the system are illustrated in FIGS. 9–11. They include a computer 72 built around a microprocessor 90 which may be a Z80 device. Internal connections for computer 72 may be made in a manner as generally taught in Petrofsky U.S. Pat. No. 4,558,704. As shown in general block diagram form in FIG. 10, microprocessor 90 is connected for reading a control program in EPROM 94 and operating in collaboration with a RAM 92.

A series of parallel ports 96 provide binary inputs from a series of control switches 111, 113, 115, 117, 68, 70, 119 and 121. Switches 68 and 70 are activated by the handicapped person on an alternating basis to initiate electrically stimulated right and left steps. Switches 111 and 113 are activated for initiation of standing and sitting sequences, while switches 115, 117, 119 and 121 are provided for sensing full extension of the knees and hips.

Analog signals representing knee flexion angles fed back from Hall effect transducers 51, 51 are supplied to ADC 98 via lines 104, 104. ADC 98 digitizes these signals as well as signals from potentiometers 101 and 105 for processing by microprocessor 90. Potentiometers 101 and 105 are provided for manual adjustment of the strength and duration of the muscle contractions initiated by closure of switches 68 and 70.

In response to signals from ADC 98 and from parallel ports 96 microprocessor 90 provides six sets of stimulation control signals to six digital-to-analog converters 100 for application to six lines 106. These signals then are applied to twelve stimulation drive circuits 108, one of which is illustrated in FIG. 11. Two stimulation drive circuits are required for each stimulated muscle group, and those drive circuits are connected to the same control line 106.

Stimulation drive circuits 108 produce electrical stimulation signals for twelve transcutaneous electrodes 172 positioned cooperatively with six grounded electrodes for stimulating the left and right gluteus maximus, hamstring and quadriceps muscle groups. However, the present invention is concerned only with the stimulation of the quadriceps muscles. This requires a total of six electrodes 172, four driven and two grounded.

For each pair of stimulation drive circuits 108 there is a common pulse generating circuit 109, as generally illustrated in FIG. 10. These pulse generating circuits generate alternating 300 microsecond pulses on output lines 122, 124 for application to the corresponding stimulation driving circuits 108. Pulse generating circuit 109 comprises three NE555 timers 110, 112 and 114. Timer 110 is used as a free running oscillator at a frequency of 40 Hz. The output of this timer triggers timers 112 and 114. Timers 112 and 114 are triggered via 0.001 microfarad capacitors 120 and 118 respectively. The trigger signal for timer 114 is also inverted by a 2N3904 transistor 116. The resulting 300 microsecond pulses on lines 122, 124 each occur at a frequency of 40 Hz and are 180 degrees out of phase with each other. These pulses are amplitude modulated by stimulation driving circuits 108 in accordance with the amplitude of the signal appearing on control line 106. A pair of cooperating stimulation drive circuits 108 produce a balanced-biphasic current controlled stimulation signal which is applied to a group of three electrodes for stimulation of a single muscle group.

Stimulation driving circuit 108 comprises four operational amplifiers 126, 128, 130 and 132, each of which may be an LF353N integrated circuit. These four amplifiers modulate the pulses provided on input line 122. The output from the fourth amplifier 132 is provided to a driving transistor 134 which may be a 2N3904 device. The output of driver 134 is provided to a D45E2 Darlington transistor, which in turn drives an RF isolation transformer 138. The output of transformer 138 is applied via a 1.0 microfarad capacitor 142 to an output line 141. The other line 143 of the transformer secondary is connected to an RF ground. This RF ground is also connected to the secondary side of the cooperating stimulation driving circuit 108 and to a shared ground electrode.

As further illustrated in FIG. 11, there is a 0.1 ohm resistor 140 in series with the primary of transformer 138. This resistor serves three functions. Firstly, it serves as a sense resistor to provide a current feedback for the operational amplifier circuit. Secondly, it enables generation of pulses which are cut off when one of the stimulation electrodes becomes opened. Thirdly, resistor 140 serves as a fuse. In the event that Darlington transistor 142 goes into a thermal runaway condition a DC bias is placed across transformer 138. This "blows" resistor 140 thereby avoiding overbiasing of the circuit and delivery of excess current.

Capacitor 142 in cooperation with a similar capacitor 142 in the corresponding paired driving circuit produces a balanced biphasic current. Preferably the current ranges from about 1 milliamphere to about 400 milliamperes. This can be adjusted by replacing resistor 140 with another resistor of a different value.

Figure 12:
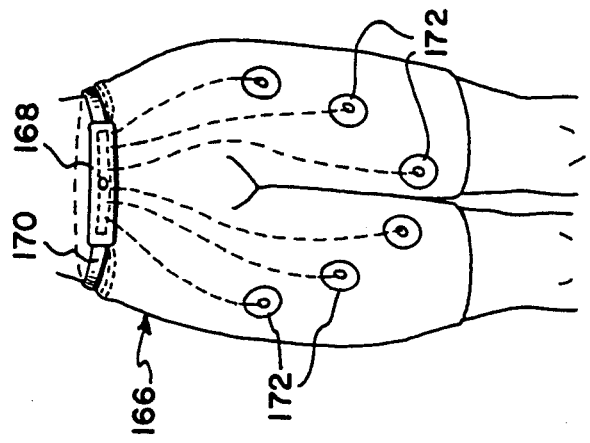
FIG. 12 is a schematic illustration of an electrode garment.

Stimulation signals from stimulation drive circuits 108 may be applied to sets of transcutaneous electrodes attached to the skin of the handicapped person as generally described in Petrofsky et al. U.S. Pat. No. 4,492,233. Alternatively the stimulation signals may be applied to sets of stimulation electrodes 172 incorporated into a garment 166, as generally illustrated in FIG. 12. Garment 166 maintains six electrodes 172 in position against the skin of the handicapped person in predetermined patterns above the quadriceps muscle groups. Lead lines from electrodes 172 extend upwardly to a common connector 168 positioned in the area of the waistband 170. Garment 166 also has other stimulation electrodes 172 (not illustrated) mounted posteriorly for positioning against the skin above the gluteus maximus muscles and above the hamstring muscles.

A flow chart for a computer routine for controlling a knee joint in accordance with the present invention is illustrated in FIGS. 13A–13D. This routine is a portion of a program written for controlling an entire walking sequence and relates only to control of a single knee joint. A similar routine is used for controlling the opposite knee joint, and each routine is executed several times during each walking step. The routine controls the amplitude of stimulation signals applied through the stimulation electrodes to the quadriceps muscles. Thus only knee extension is commanded. Flexion of the knee occurs during walking as a natural effect of gravity, and it is not necessary to stimulate any flexing movement by the knee.

It will be appreciated that the embodiment of the invention as herein described stimulates the quadriceps muscles of each leg in synchronism with stimulation of the gluteus maximus muscles and the hamstring muscles for the opposite hip. Such stimulation produces a reciprocatinggait walking motion. However, the knee control routine of the present invention may be used with other walking assistance techniques, as for instance, the walking assistance technique taught in Petrofsky et al. Ser. No. 671,805.

The flow chart of FIGS. 13A–13D refers to several variables as follows:

SINC 2—a control variable representing a desired knee flexion angle. In general, this variable may range from 0 to 127 corresponding to flexion angles ranging from 0 (knee lock) to −90°. Positive knee angles (hyperextension) are never commanded. A desired sequence of knee angles is stored in memory, and values thereof are transferred at appropriate times into the memory location designated SINC 2.

FLAG 8 designates a memory location in which is stored a number representing the difference between the desired knee angle and the actual knee angle as measured by a knee sensor and transmitted to the computer.

FLAG 1 designates a memory location in which is stored a number which is incremented to provide a command delay. This is required because a computer operates much faster than the human muscles being controlled. After each knee stimulation command, the computer waits an appropriate period of time before measuring the knee response and generating a new stimulation command.

FOFO 3 is a flag which is set to a value of 1 each time the stimulation level is increased. So long as FOFO 3 has a value of 1, further increases in stimulation are inhibited until such time as FLAG 1 has been incremented to 0. At that time FOFO 3 is reset to 0 for enabling another increase in the stimulation level.

FOFO 6 is a variable which indicates a value range for the error stored in FLAG 8.

T3 is a storage location for the desired stimulation level. Stimulation is accomplished by reading the value of this location and transferring that value out through port 114.

Figure 13A:
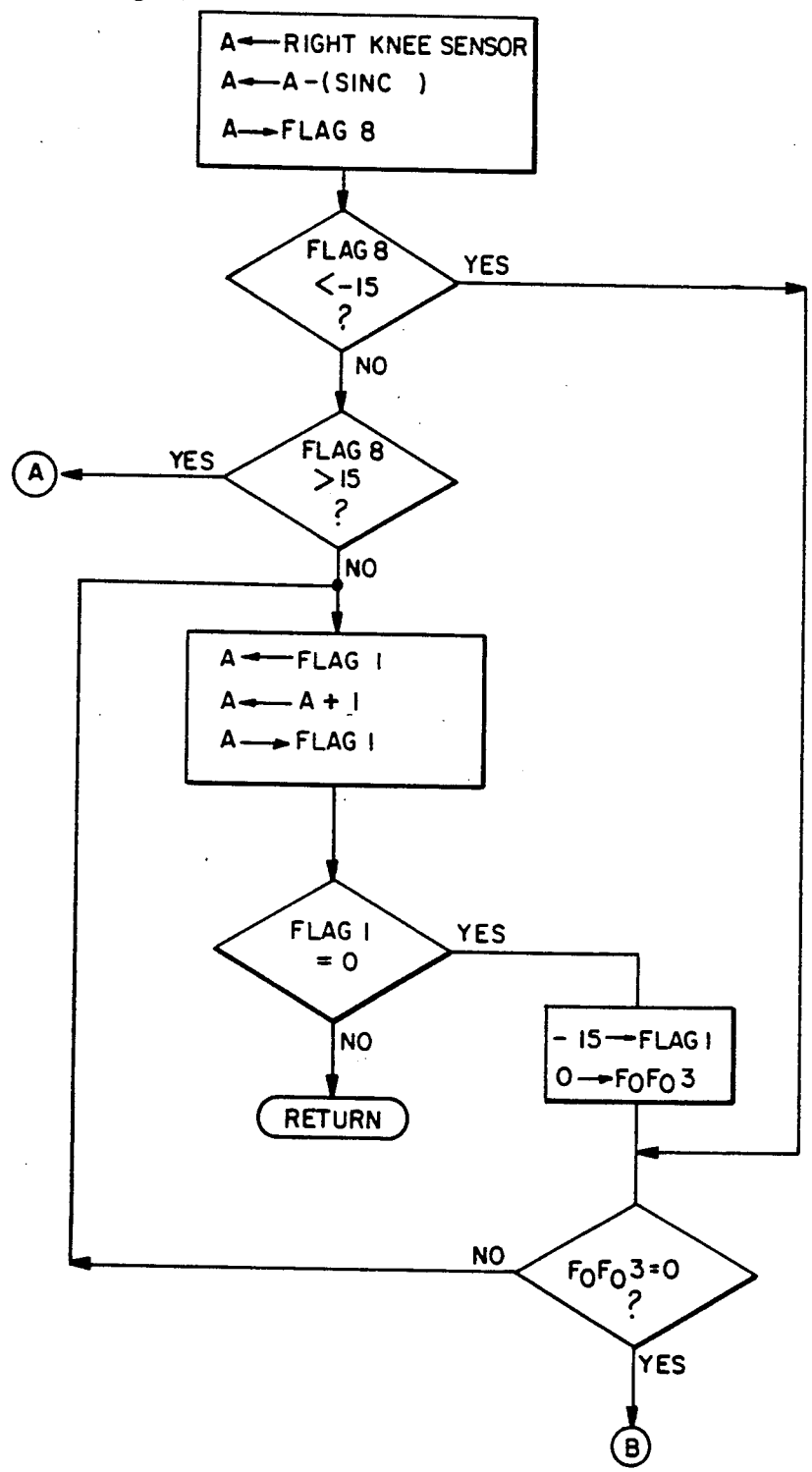
FIG. 13A through 13D are a flow chart for a computer program for knee joint control.
Figure 13B:
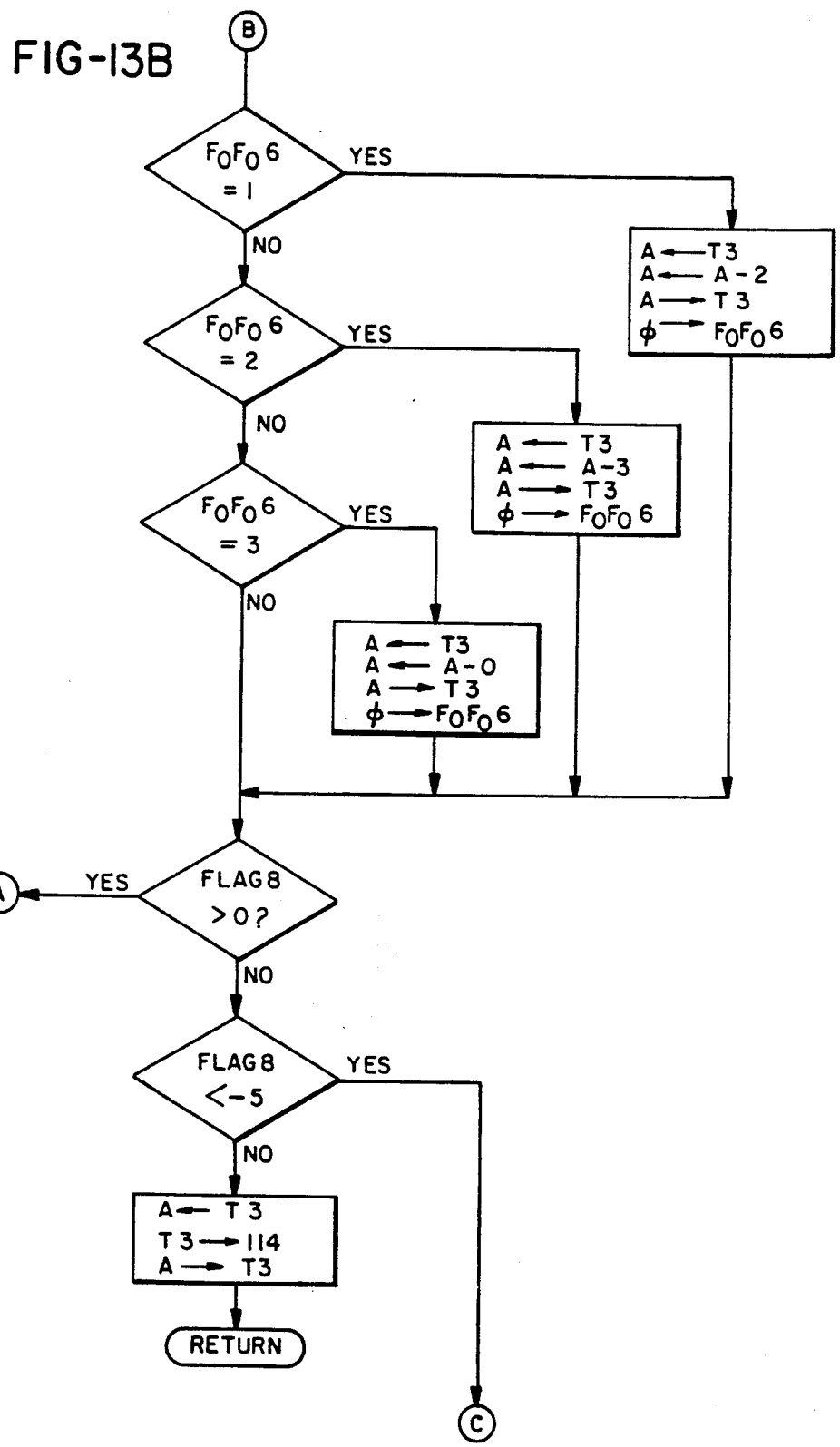

As illustrated in FIG. 13A, the knee control routine commences by reading the knee sensor, comparing the sensor value with the contents of memory location SINC 2 and storing the difference in FLAG 8. In this regard, it will be appreciated that the designation A refers to the accumulator register of the microprocessor. Also the scaling factor is such that 15 units are equivalent to about 10.6°.

After the knee error angle has been read into FLAG 8, the program performs a pair of tests to determine whether the error is in the range between −10.6° and +10.6°. If it is, then the program increments FLAG 1 and then checks its value to determine whether or not the required delay time has elapsed since the last stimulation adjustment. If FLAG 1 is equal to Zero, the program adjusts the flag to a value of −15 and proceeds to adjust the stimulation level as appropriate. Otherwise there is a return to the main program.

If the error stored in FLAG 8 is less than −15 units (10.6° of excess flexion), then the program checks the contents of location FOFO 3. If this register has the value of 0, it means that there was a very small error during the last program loop. This could indicate that the knee is collapsing, and the FLAG 1 delay loop is bypassed. In the usual case for values of FLAG 8 less than −15 the program makes a normal pass through the delay loop.

Figure 13C:
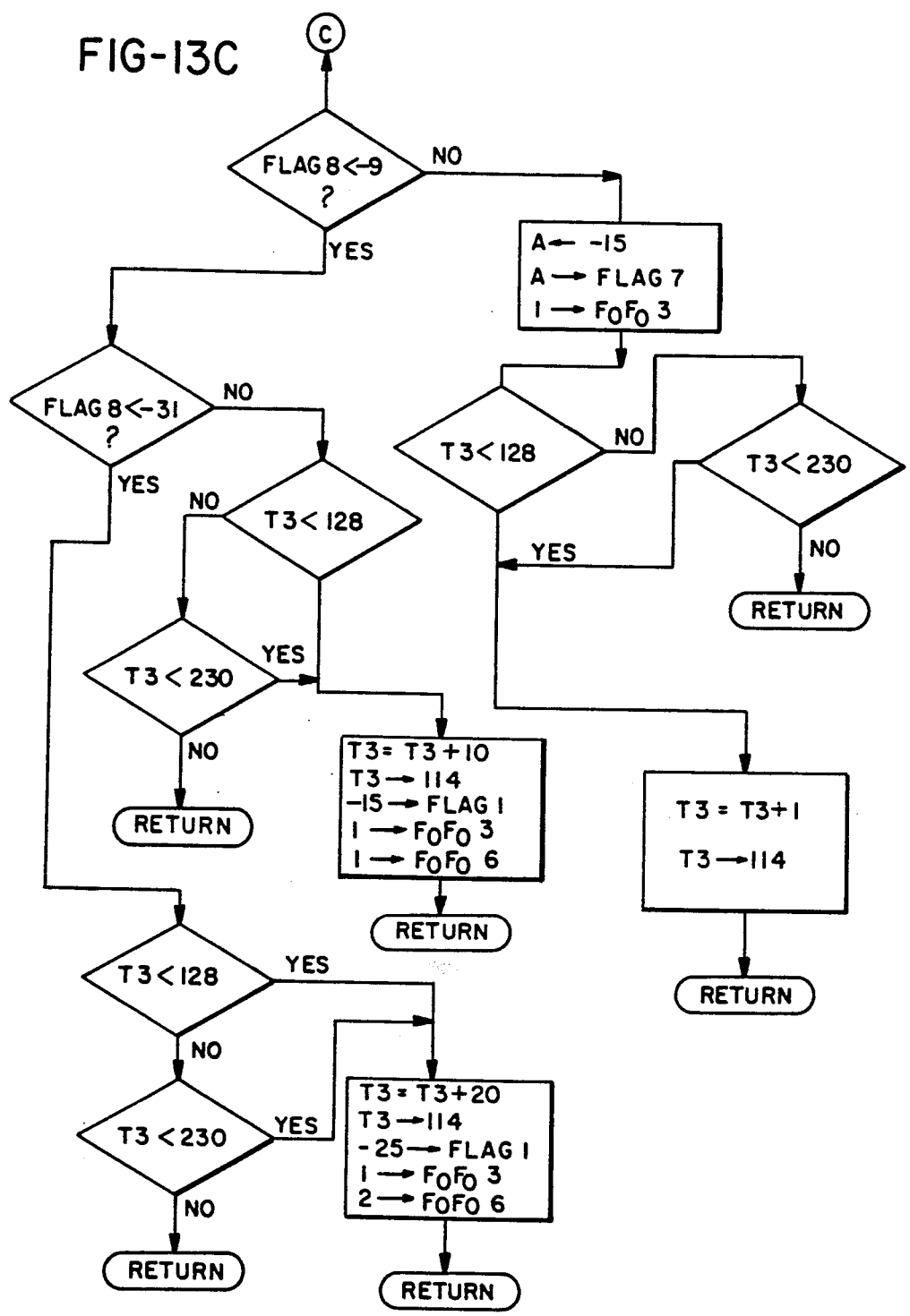
Figure 13D:
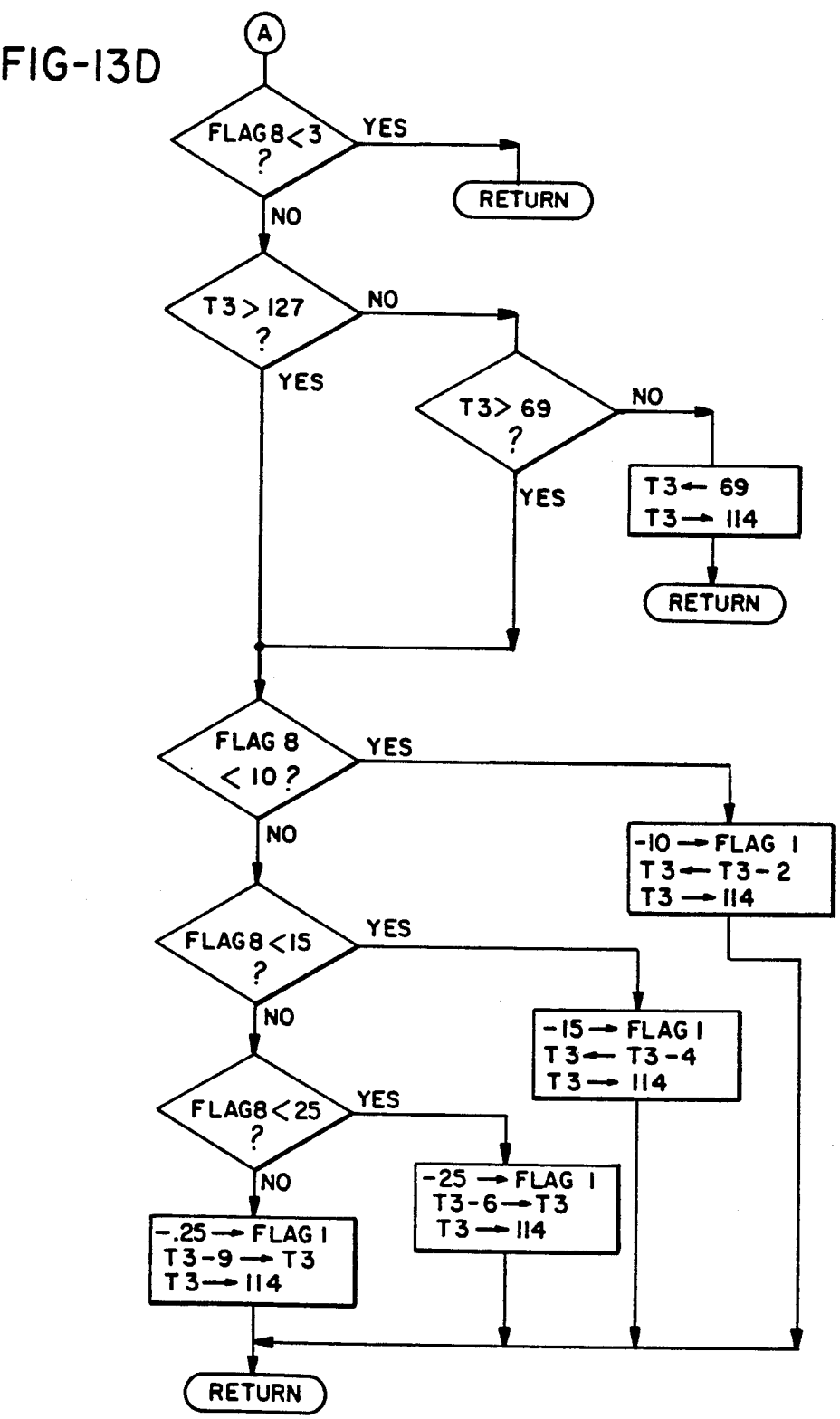

If the check of FLAG 8 indicates the knee is extended more than 10.6° beyond the desired value (as indicated by a number greater than +15 being stored in FLAG 8), then the program branches to the subroutine illustrated on FIG. 13D. Otherwise, the program proceeds in ordinary course to the sequence illustrated on FIG. 13B. As shown on that figure, the program checks the value of FOFO 6 which indicates the amount of excess knee flexion at the time of the last upward adjustment of stimulation. A value of 1 in this register indicates that the previous excess flexion ranged between 6.4° and 22°. If the excess flexion was in that range, then the stimulation control number stored in register T3 is decreased by 2 units. This will cause a corresponding decrease in stimulation during the current pass through the routine, unless there is still more than about 3.5° of excess flexion. The stimulation level is similarly decreased by 3 units if the value of FOFO 6 indicates an excess flexion greater than 22° at the time of the last upward stimulation adjustment. If the excess flexion at the time of the last upward adjustment in stimulation level was less than 6.4°, then value of FOFO 6 will be 0, and no adjustment will be made to the contents of register T3 during passage through that portion of the program illustrated in FIG. 13B.

After the program checks the value of FOFO 6, it proceeds to check the value of FLAG 8. If FLAG 8 is greater than 0, this indicates that the stimulation level is too high, and the program branches to the subroutine of FIG. 13D for appropriate downward adjustment thereof. If FLAG 8 has a value between 0 and −5, this indicates an excess flexion ranging between 0 and 3.5°, an amount considered too small to require a stimulation increase. For values in this range, the contents of register T3 are simply transferred to output port 114 for stimulation at the corresponding level. If it should happen that SINC 2 has a value of 0 at that time, then the opening angle of hinge assembly 24 will be less than 3.5°. Thus the knee will be nearly straight and the gravity lock will be operative. Therefore no increase in the stimulation level is required in order to produce locking of the knee. This then avoids the end looping problem which was mentioned above.

If FLAG 8 indicates that the knee is flexed at least 3.5° more than it should be, then the program proceeds to perform a logical sequence as outlined on FIG. 13C. Entry into this portion of the routine occurs only when the stimulation level being applied to the quadriceps muscle group is too low, thereby permitting excess flexion. This portion of the routine causes appropriate upward adjustment of the stimulation level and resets FLAG 1 and register FOFO 3. If the excess flexion is greater than about 22° (FLAG 8 less than −31), then the stimulation level is increased by 20 units, and a value of 2 is set into register FOFO 6 for use during the succeeding program loop. For excess flexion ranging between 6.4° and 22° the stimulation level is increased by 10 units and FOFO 6 is set to a value of 1. If the flexion error is between 3.5° and 6.4°, then the stimulation level is increased 1 unit and no change is made to the contents of register FOFO 6 (i.e. remains at 0). As noted above, the program does not enter this portion of the routine for flexion errors smaller than 3.5°. Irrespective of the flexion error the contents of register T3 are not increased, if the value therein is already greater than 230. This ensures that the stimulation level will not exceed 250 and cause an accumulator overflow.

In the event of excessive stimulation and consequent entry into the subroutine illustrated in FIG. 13D, the program makes an initial check to determine the value of the excess extension. If it is less than 2.1°, (FLAG 8 less than 3), then there is a return to the main program without any adjustment of stimulation level. If the excess extension exceeds 2.1° and the stimulation level is less than 69 units, then the stimulation is adjusted to a level of 69, and a return is made to the main program.

If the stimulation level exceeds 69 units, then a further check is made on the value of the excess knee extension. For excess extension ranging between 2.1° and 7.1° the stimulation level is decreased by 2 units, and FLAG 1 is adjusted to produce a program delay of 10 loops during the succeeding passage through that portion of the routine illustrated in FIG. 13A. An excess knee extension ranging between 7.1° and 10.6° causes a downward adjustment of 4 stimulation units and a program delay of 15 loops. If the excess knee extension ranges between 10.6° and 17.1°, then the stimulation level is decreased by 6 units and the program delay is set for 25 loops. An excess extension exceeding 17.7° causes a stimulation decrease of 9 units and a program delay of 25 loops.

What is claimed is:

1. Apparatus for stimulated control of a knee joint in a paralyzed human leg comprising:
    a brace for said leg; said brace being provided with an over-center hinge which opens when said knee joint flexes and which tends to lock under a vertically applied load if opened less than a first predetermined angle when said load is applied,
    a sensor for sensing the angle of opening of said hinge and generating a sensing signal indicative thereof,
    control means connected for receiving said sensing signal, generating a reference signal representing a desired value for said angle of opening, and generating a command signal related to the difference between said sensing and said reference signal; said command signal being non-responsive to changes in said sensing signal when said angle of opening is less than a second predetermined angle which is greater than zero and not greater than said first predetermined angle, and
    stimulation means responsive to said command signal for stimulating muscles of said leg connected for causing extension of said knee joint.

2. Apparatus according to claim 1 wherein said first predetermined angle in an angle of about 6°.

3. Apparatus according to claim 2 wherein said second predetermined angle is an angle of about 3.5°.

4. Method for controlling flexion of a human knee during stimulated walking comprising the steps of:
    (1) attaching to said knee a brace having an over-center hinge which opens when said knee flexes and which tends to lock under a vertically applied load, if opened less than a first predetermined angle when said load is applied,
    (2) applying electrical stimulation signals to the quadriceps muscles for said knee to support the the body weight of the person who is walking,
    (3) sensing the angle of opening of said hinge
    (4) comparing said angle of opening with a desired flexion angle for said knee,
    (5) increasing the stimulation activity of said stimulation signals when said opening angle exceeds said desired angle by an amount which is more than a second predetermined angle; said second predetermined angle being greater than zero and not greater than said first predetermine angle and
    (6) maintaining the stimulation activity of said stimulation signals without change when said opening angle exceeds said desired angle by an amount which is less than said second predetermined angle.

5. Method according to claim 4 wherein a delay is interposed between said comparison and said increase of stimulation activity.

6. Method according to claim 5 including the step of classifying the difference between said angle of opening and desired angle according to error range; said increase being made in accordance with said error range.

7. Method according to claim 4 wherein said attaching step comprises the step of attaching to said knee a brace having an over-center hinge which opens when said knee flexes and which tends to lock under a vertically applied load, if opened, less than about 6° when said load is applied.

8. Method according to claim 7 wherein said increasing step comprises the step of increasing the stimulation activity of said stimulation signals when said opening angle exceeds said desired angle by more than about 3.5°.

* * * * *